United States Patent [19]

Bronstert

[11] Patent Number: 5,171,800
[45] Date of Patent: Dec. 15, 1992

[54] ANIONIC POLYMERIZATION WITH BIFUNCTIONAL INITIATORS

[75] Inventor: Klaus Bronstert, Carlsberg, Fed. Rep. of Germany

[73] Assignee: BASF Aktiengesellschaft, Ludwigshafen, Fed. Rep. of Germany

[21] Appl. No.: 538,083

[22] Filed: Jun. 13, 1990

[30] Foreign Application Priority Data

Jun. 28, 1989 [DE] Fed. Rep. of Germany ....... 3921140
Aug. 16, 1989 [DE] Fed. Rep. of Germany ....... 3926925

[51] Int. Cl.$^5$ .............................................. C08F 4/46
[52] U.S. Cl. .................................. 526/173; 526/180; 526/181; 525/250; 525/314
[58] Field of Search ............... 526/173, 77, 180, 181; 525/250, 314

[56] References Cited

U.S. PATENT DOCUMENTS

| | | | |
|---|---|---|---|
| 3,296,150 | 1/1967 | Kahle | 526/173 X |
| 3,377,404 | 4/1968 | Zelinski | 526/173 X |
| 4,181,684 | 1/1980 | Sigwalt et al. | 526/173 X |
| 4,861,742 | 4/1989 | Bronstert et al. | 526/173 X |
| 5,089,572 | 2/1992 | Marchand et al. | 526/77 |

FOREIGN PATENT DOCUMENTS 1499467 2/1978 United Kingdom .
2112787 7/1983 United Kingdom .

Primary Examiner—Fred Teskin
Attorney, Agent, or Firm—Oblon, Spivak, McClelland, Maier & Neustadt

[57] ABSTRACT

An organic compound of an alkali metal, of the formula I

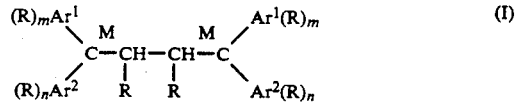

which is obtained by reaction of an appropriate diarylethylene of the formula II with an alkali metal (M), especially lithium,

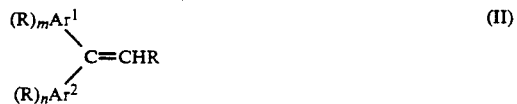

where $Ar^1$ and $Ar^2$ are identical or different aryl or hetaryl radicals which have one or more rings which are either separate or fused, and where R is at least one substituent different from hydrogen and which is chemically inert to the alkali metal or its alkyl, with the proviso that the total of the carbon atoms in all the R is at least 3, and m and n are each an integer up to 4, is used for the preparation of polymers whose monomers are amenable to anionic polymerization.

2 Claims, No Drawings

ANIONIC POLYMERIZATION WITH BIFUNCTIONAL INITIATORS

Organic compounds of alkali metals are used as initiators for anionic polymerization of, preferably, alkenylaromatic compounds and/or dienes. Lithium alkyl is particularly suitable, being comparatively stable and, in contrast to the corresponding sodium or potassium alkyl, being also soluble in hydrocarbons and thus permitting polymerization in a hydrocarbon solvent. Living polymers with lithium end groups can be converted with suitable reagents into terminally functionalized polymers in high yield, for example into those with —OH, —SH or amino groups. These reactions take place most satisfactorily when the reaction medium is mainly composed of hydrocarbons.

Whereas the known monofunctional lithium alkyls meet all the requirements as initiators for anionic polymerization, the known bifunctional initiators have deficiencies. Such bifunctional initiators, especially those low in or free of ethers, are required, for example, when it is wished to generate from dienes polymers which are functionalized at both ends of the chain and preferably contain the diene incorporated in the 1,4 configuration.

Bifunctional Lithium initiators are prepared, for example, by addition of lithium onto fused aromatic ring systems such as naphthalene, biphenyl etc. or polyaryl-substituted ethylenes such as 1,1-diphenylethylene or stilbene (U.S. Pat. No. 3 170 903). This addition takes place only in the presence of ethers or other polar solvents whose presence adversely affects the polymerization of dienes because, in this case, the diene is mainly incorporated in the 1,2 or 3,4 configuration.

Polymers with the diene in the 1,2 or 3,4 configuration have less desirable properties, including a high glass temperature, oxidation sensitivity, susceptibility to crosslinking and low thermal stability during processing. However, attempts to remove the ether from the initiators results in them losing all or part of their activity and/or becoming insoluble.

To overcome these disadvantages, it has been proposed, by P. Zelinsky in U.S. Pat. No. 3 377 404, that the dilithium initiators which have initially been produced by reaction of polyhalogen compounds, fused polyaromatics or polyarylated ethylenes with ethers be, in a second reaction stage, solubilized by addition of diolefins and only then be distilled to remove the ether.

Although the initiators formed in this way are soluble in hydrocarbons, a partial decomposition is observed during their preparation, so that polymers prepared therewith are now only partly polyfunctional.

Other bifunctional initiators are generated by addition of Li alkyl onto starting compounds which contain 2 double bonds. These initiators often contain undesired monofunctional fractions or are insufficiently active, reacting incompletely to produce polymers with a molecular weight distribution which is too high and undesirably wide.

L. J. Morton and M. Fetters (U.S. Pat. No. 3 663 634 and Macromolecules, 2 (1969) 453 et seq.), finally, use 1,4-di-lithium 1,1,4,4-tetraphenylbutane, which is prepared by reacting 1,1-diphenylethylene with metallic lithium in a mixture of 15% anisole and 85% cyclohexane, as bifunctional initiator. The preparation takes place extremely slowly (2 days or longer) and incompletely, and only very low concentrations of initiator can be obtained. Furthermore, the initiator is insoluble in hydrocarbons and therefore has to be initially solubilized with isoprene, resulting in an isoprene polymer as byproduct, before polymerization can be carried out in cyclohexane or benzene (Macromolecules 2 (1969) 454, column 1, 3rd paragraph). Finally, the presence of anisole in turn results in a considerable increase in the 1,2 or 3,4 configuration when butadiene or isoprene is incorporated.

It was therefore an object of the present invention to provide initiators for anionic polymerization, which are readily soluble in media composed wholly or mainly of hydrocarbons, are stable and are free of monofunctional fractions, a straightforward process suitable for the preparation thereof, and the use of these catalysts for the preparation of polymers which may be functionalized and which show growth at both ends of the chain and have a narrow molecular weight distribution and approximately the molecular weight expected from calculation.

We have found that this object is achieved by an organic compound of an alkali metal, of the formula I

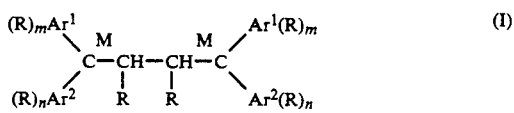

which is obtained by reacting an appropriate diarylethylene of the formula II with, in particular, lithium or another alkali metal (M)

where $Ar^1$ and $Ar^2$ are identical or different aryl or nitrogen-containing heteryl radicals which have one or more rings which are either separate or fused, and where R is at least one substituent different from hydrogen and which is chemically inert to the alkali metal or its alkyl, with the proviso that the total of the carbon atoms in all the R is at least 3, and m and n are each an integer up to 4.

The reaction is carried out in an ether or tertiary amine. The resulting di(alkali metal) compound is used as initiator, if necessary after removal of the ether or tertiary amine.

$Ar^1$ and $Ar^2$ in formula I or II are identical or different aromatic, including poly- or heterocyclic, ring systems which may contain nitrogen, sulfur or oxygen. Possible examples of $Ar^1$ and $Ar^2$ are phenyl, naphthyl, biphenylyl, phenanthryl, anthryl, phenoxyphenyl, pyridyl, quinolyl etc. $Ar^1$ and $Ar^2$ are each preferably phenyl or naphthyl.

R is hydrogen or, for example, linear or branched alkyl, aralkyl or cycloalkyl which has 1 or 7 or 5 to 25 carbon atoms and can also contain chemically inert components such as ether bridges or tertiary amino groups. The substituents may furthermore form annular bridges with $Ar^1$ or $Ar^2$, but these must have at least three aliphatic carbon atoms to meet the requirement for solubility.

Overall, in order to obtain satisfactory properties, at least one R must be different from hydrogen, and the total of carbon atoms in all the R must be at least three. In general, no more than 30, in any event no more than 60, carbon atoms are required in the R substituents, although more extensive substitution is not deleterious.

In general there is an increase in the number of carbon atoms necessary for adequate solubility from aromatic solvents, e.g. benzene or toluene, via alicyclic, e.g. cyclohexane or methylcyclohexane, to purely aliphatic solvents, e.g. n-hexane, n-heptane or iso-octane.

The increase in the solubility of the initiators in hydrocarbons is inadequate with fewer than 3 carbon atoms in the substituents. If the intention is to prepare diene polymers or copolymers in solvents which contain very little or no ethers (0 to 3 moles of ether per mole of lithium active in the polymerization), the initiators ought to have substituents containing more than 4 carbon atoms.

Among substituents R with the same number of carbons, those with a less branched structure have a better solubilizing action than more highly branched substituents. Thus, for example, an initiator derived from 1,1-diphenylethylene which has n- or iso-butyl on one benzene nucleus is more soluble in hydrocarbons than is one with a t-butyl group or one in which two substituents form a ring of 4 methylene groups (tetralin structure). structure).

Preferred $Ar^1$ and $Ar^2$ are phenyl and naphthyl, and the aliphatic (formula I) or olefinic (formula II) moiety is preferably unsubstituted (R=H) and, moreover, the substituents, which may total up to 8, are (apart from hydrogen) methyl, linear or branched alkyl, cycloalkyl, dialkylamino and/or alkoxyalkyl with a total of more than 3 to 30 carbon atoms, i.e. compounds of the formula II are derivatives of 1,1-diphenylethylene or 1-phenyl-1-(1-naphthyl)ethylene which have on each of the aromatic nuclei 1 to 4 aliphatic substituents which may contain tertiary nitrogen and together contain more than 3 but less than 30 carbon atoms.

Examples of particularly suitable and readily obtainable compounds of the formula II are 1,1-diphenylethylenes which are alkylated in the nucleus or in the 2 position, or mixtures thereof (formula IIa)

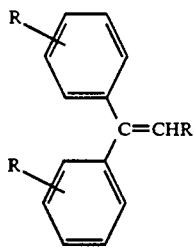
(IIa)

and derivatives of 1-phenyl-1-(1-4-naphthyl)ethylene, 1-phenyl-1-(2-4-pyridyl)ethylene and other derivatives of ethylene such as

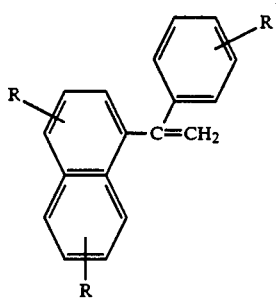

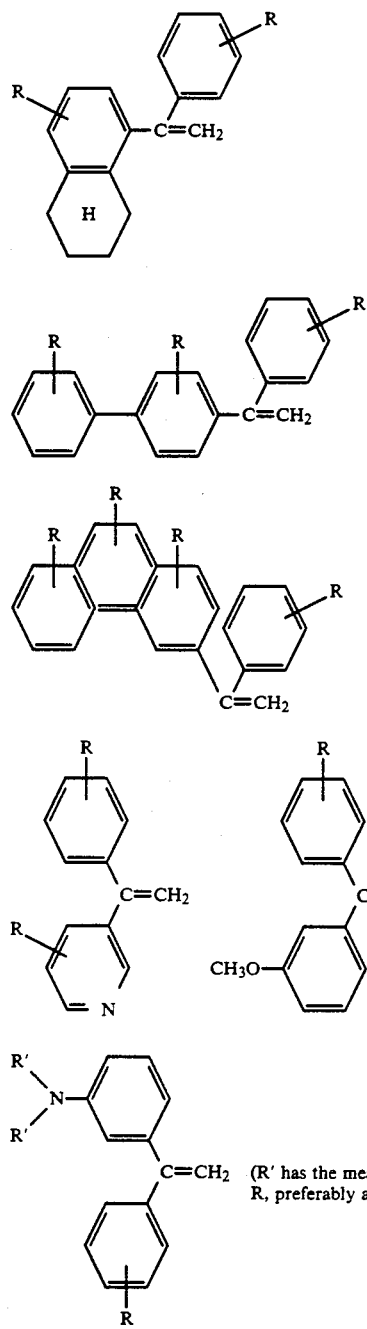

(R' has the meaning of R, preferably alkyl)

It can be assumed that the preparation of substituted diphenylethylenes is known. An example of a very useful method is the reaction of suitable acetophenones, or benzophenones, with unsubstituted or substituted phenylmagnesium bromide, or methylmagnesium or alkylmagnesium bromide, and dehydration of the resulting diphenylalkylcarbinols.

The metallation and dimerization of the 1,2-diarylethylenes according to the invention takes place with evolution of heat when they are reacted with lithium in the presence of an ether, a tertiary amine and, where appropriate, an aliphatic, alicyclic and/or aromatic solvent at from −70° to +70° C., preferably from 0 to 40° C. One advantage is that complete conversion is achieved in the presence of comparatively small amounts of polar solvents. The amount of ether or tertiary amines in the reaction mixture ought, however, to be greater than 3 mol per mol of substituted 1,1-diarylethylene in order to ensure complete conversion.

Examples of particularly suitable aliphatic ethers are dimethyl ether, diethyl ether, dipropyl ether, dibutyl ether, diisopropyl ether, t-butyl methyl ether etc. and alicyclic ethers such as tetrahydrofuran etc. Examples of suitable tertiary amines are trialkylamines such as triethyl-, trimethyl- or dimethylethylamine etc., and alicyclic or aliphatic/aromatic amines such as N-methylpiperidine or dimethylaniline. The reaction takes place rapidly even at room temperature and is often complete after 15 to 60 minutes, the conversion generally being more than 95% by weight of the starting compound. If less suitable aromatic ethers such as anisole or phenetole are used, the reaction takes correspondingly longer. Undesired side reactions then result in the metal content in the reaction medium often being considerably higher than the content of alkali metal active in the polymerization.

Because the low density of lithium means that it floats on the surface, efficient mechanical mixing of the reaction medium is expedient for rapid reactions.

Initiator solutions prepared in this way can be used directly, without removal of the polar solvent, for many purposes, e.g. if the intention is to hydrogenate butadiene polymers prepared with their aid, and the hydrogenation product is not required to crystallize.

Where ether-free initiators are required, volatile ethers or amines are used and can be removed after the metallation by distillation under reduced pressure. The temperature should not exceed 70° C., preferably 35° C. It is expedient to add to the ether or amine a hydrocarbon which has a higher boiling point than the latter.

Low-boiling aliphatic ethers, e.g. dimethyl ether, diethyl ether, diisopropyl ether or t-butyl methyl ether, or low molecular weight tertiary amines such as triethylamine, can be removed without difficulty to a residual content of less than 0.1 mol per mol of lithium active in the polymerization. The solubility of the initiators according to the invention is usually retained as long as at least 2 mol of ether are present per mol of lithium alkyl active in the polymerization. If the ether is completely removed by distillation from initiators which have been prepared from 1,1-diphenylethylene with substituents containing 3 or 4 carbon atoms they may, depending on the solvent, become sparingly soluble and precipitate partially or completely.

Initiators obtained from 1,1-diarylethylenes with long, mainly linear or only slightly branched, alkyl groups and containing more than 6 carbon atoms in the substituents R remain in solution in all solvents. The minimum size of the substituents also depends on the radicals Ar. It must be determined for each case individually.

Solutions of initiators which contain little or no alicyclic or aliphatic ethers or tertiary amines result in predominantly 1,4-polymerization of dienes. The resulting polymers usually have a wider molecular weight distribution and higher molecular weights than when monofunctional initiators are used, in which case the experimental molecular weights agree relatively well with those calculated from the monomer/catalyst ratio.

Impurities must be removed from all solvents and starting materials before their use. A suitable example is distillation over a metal alkyl such as aluminum triethyl under an inert gas atmosphere, e.g. under dry, oxygen-free nitrogen or argon.

Reaction of the substituted 1,1-diarylethylenes to be used according to the invention with alkali metal results in 1,4-dialkali metal 1,1,4,4-tetraarylbutane derivatives which are intensely colored in solution. The color varies, depending on the starting material, from dark brown to bluish black.

Scarcely any lithium-consuming side reactions take place during the preparation of the initiators Each mol of 1,1-diarylethylene used results in about 1 mol of molecular centers active in the polymerization; this polymerization activity, called PA hereinafter, can be determined by titrating the solution against i-propyl alcohol under inert conditions until it becomes colorless. The PA generally agrees well with the alkali metal content of the solution.

The initiators according to the invention are outstandingly suitable for the polymerization of vinyl aromatic compounds such as styrene and its derivatives substituted by alkyl in the nucleus and/or in the $\alpha$ position, and of conjugated dienes such as butadiene, isoprene, 2,3-dimethylbutadiene, piperylene etc. The polymerization can take place in all the solvents which are used for monofunctional initiators. Besides hydrocarbons, also suitable as solvents are aromatic compounds such as benzene or toluene, but these may have disadvantages, e.g. benzene is physiologically unacceptable and toluene has a chain-transfer action, which aliphatic solvents such as cyclohexane or hexane etc. do not have.

Solvents low in or free of ethers must be used for polymerization of diolefins to achieve a high proportion of the 1,4 configuration. In such cases the start of polymerization is more difficult than with monofunctional initiators, but is distinctly better than with known bifunctional initiators. At an elevated starting temperature there are produced, with good catalyst yields, bifunctionally growing polymers with a somewhat wider molecular weight distribution than is obtained with monofunctional initiators, and with a molecular weight Mn which is higher than expected by calculation. Moreover, 2 polymer peaks are sometimes found. The molecular weight distribution becomes narrower on polymerization in the presence of 0.1 to 1 mol per mol of PA of an aliphatic lithium alcoholate (U.S. Pat. No. B 4 754 329, EP-A-210 016) or of lithium halides. These additives do not affect the configuration of diolefin incorporation.

The start of polymerization of diolefins and vinylaromatic compounds is facilitated in the presence of small amounts, e.g. 0.5 to 6 moles per mole of PA, of ethers or tertiary amines. The resultant polymers then have a narrow molecular weight distribution and approximately the molecular weight calculated from the monomer/initiator ratio as in anionic polymerization with monofunctional initiators. However, in the presence of the ethers or amines, there is incorporation of the dienes with an increased proportion, depending on the amount thereof, of 1,2 or 3,4 configuration into the polymers. This may be advantageous, for example when the polymers are to be hydrogenated. In order that the hydrogenation products do not crystallize and have a low glass point, as is desired for telechelic polymers, the proportion of 1,2-incorporated butadiene must be raised to about 40 to 50%. About 1 to 2 moles of THF per mole of PA are required for this.

Three-block copolymers can be prepared in fewer steps with bifunctional than with monofunctional initiators. For example, consecutive polymerization of butadiene and styrene results, in 2 steps, in 3-block copolymers whose properties correspond to those polymers of the same composition prepared by conventional 3-step polymerization methods with monofunctional catalysts

Evidence of the bifunctional growth of block copolymers prepared with catalysts according to the invention is that, after oxidative degradation of the polybutadiene moiety with osmium tetroxide (cf. Angew. Makromol Chem. 26 (1972) 207), the remaining polystyrene blocks have in both cases the molecular weight expected for 3-block copolymers.

The corresponding sodium or potassium initiators according to the invention are less soluble in hydrocarbons. Nevertheless, they can also be used to polymerize, for example, styrene in cyclohexane or other hydrocarbons. However, the resultant molecular weight distributions are wider than with lithium initiators.

The viscosity of the living polymer solutions prepared with initiators according to the invention is, at the same molecular weight, higher than that of living polymers prepared with monofunctional initiators, because the polar, ionic chain ends associate reversibly to form a physical network. The association increases with decreasing ether content in the solvent mixture. It is enhanced to such an extent by conversion of the carbanionic end-groups with terminating reagents into, for example, lithiated carboxyl, carbamoyl, hydroxyl or mercapto end-groups that even at low polymer concentrations and molecular weights there is formation of a clear gel-like mass. The mass can be mixed with high stirring energy and high torque until conversion is complete. Addition of water, alcohol or other compounds containing active hydrogen to this gel abolishes the apparent (ionic) crosslinking, and the viscosity of the solution decreases by several orders of magnitude.

Functionalization of the living polymers which have been prepared with initiators according to the invention and have grown at both ends of the chain is possible, in particular, in high yield in the absence or presence of only a small amount of polar solvent. Reactions for functionalizing the living ends of the chain are known. Examples of suitable functionalizing reagents are oxiranes which provide terminal primary or secondary hydroxyl groups (cf. U.S. Pat. No. B 3 786 116), or thiiranes which can be used to introduce terminal mercapto groups. Polymers which contain at least one amino group at the end of the chain can be obtained by the method of EP-A-0 211 395 or European patent application 87 103 893.1. The reactions have been described in detail, and some of them are to be found in the examples which follow.

Polymers according to the invention which have been built up entirely or partly from dienes can be hydrogenated. The hydrogenation is carried out with molecular hydrogen and catalysts based on metals or metal salts of the 8th subgroup of the periodic table, either in homogeneous or in heterogeneous phase. The processes are known and are described, for example, in U.S. Pat. No. B 3 113 986, DE-B-1 222 266, DE-A-2 013 263, DE-B-1 106 961 or DE-A-1 595 345.

Polymers functionalized at both ends of the chain with mercapto, hydroxyl or amino groups are of particular interest as prepolymers for polyurethanes, epoxy resins and other resins or for modification thereof. The preparation of epoxy resins and of elastomeric polyurethanes composed of a "hard segment" of aromatic polyisocyanates and a "soft segment" of functionalized flexible macromolecules is known and is described by H. P. Elias in Makromoleküle, pages 778 to 780 and 809 to 812, 4th ed. (1981), Hüttig und Wepf Verlag, Basel-Heidelberg-New York and the literature cited therein.

Functionalized polymers which have been prepared according to the invention from dienes and/or from vinylaromatic compounds and which contain amino or hydroxyl groups at the ends of the chain can be crosslinked, for example, with diisocyanates and other reagents. Solutions of such polybutadienes mixed with diisocyanates, poured onto silicone-coated paper and dried yield, when the polymers are predominantly built up of dienes, elastic, dry films which are insoluble in hydrocarbons and which can be detached from the substrate and have high reversible extensibility.

Polybutadienediols are distinguished as "soft segments" in thermoplastic polyurethanes by particularly good separation of "hard and soft segments", which is desirable for particular applications and processing techniques, as is described by Becker and Braun, Kunststoffhandbuch, volume 7, Polyurethane, page 33 (1983), 2nd ed., Hanser Verlag, Munich-Vienna. At the same weight average molecular weight, oils prepared according to the invention have, because of their narrow molecular weight distribution, a lower viscosity than known prepolymers, e.g. radical-polymerizing telechelic polybutadiene oils, polytetrahydrofuran or polyesters. They are therefore more readily processed.

Polymers obtained according to the invention generally have average molecular weights (weight average $\overline{M}_w$) of from 500 to 500,000, preferably 3000 to 130,000, determined by gel permeation chromatography (GPC) and comparison with standardized polymers suitable for calibration (cf. G. Glöckner, "Polymercharakterisierung durch Flüssigkeitschromatographie", Verlag A. Hüthig, Heidelberg (1982)). Measurements are carried out in 0.25% by weight tetrahydrofuran solution at 23° C. and a flow rate of 1.2 ml/min. The molecular mass is expediently determined before functionalization because some functionalized polymers are adsorbed on GPC columns and make them unusable.

The polymers are worked up in a conventional manner, e.g. by precipitation with a nonsolvent, by removal of the solvent by distillation, or by steam distillation. Degassing on a degassing extruder is also possible.

The following substituted 1,1-diarylethylenes were used as starting materials in the examples.

TABLE 1

| No. | Structure | B.p. °C. | Preparation |
|---|---|---|---|
| A | 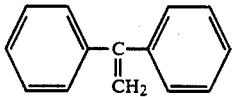 (comparison) | — | Available from Janssen Chimica |
| B | 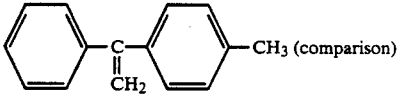 (comparison) | 106° C. 0.06 mbar | Phenylmagnesium bromide + 4-methylacetophenone ⟶ dehydration |
| C | 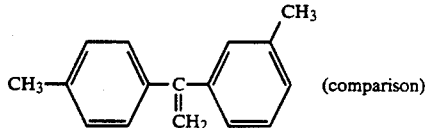 (comparison) | 102–110° C. 0.04 mbar | Phenylmagnesium bromide + 3-methylacetophenone ⟶ dehydration |
| D | 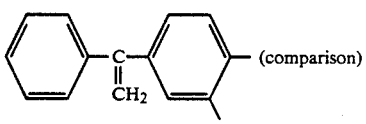 (comparison) | 125–134° C. 0.1 mbar | Phenylmagnesium bromide + dimethylacetophenone ⟶ dehydration |
| E | 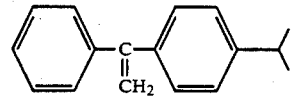 | 121–133° C. 0.05 mbar | Phenylmagnesium bromide + 4-isopropyl-acetophenone ⟶ dehydration |
| F | 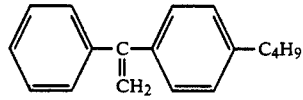 | 135–155° C. 0.05 mbar | Phenylmagnesium bromide + 4-butylacetophenone ⟶ dehydration |
| G | 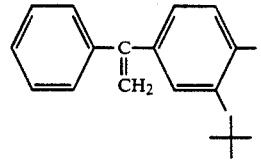 | 122–142° C. 0.05 mbar | Phenylmagnesium bromide + 4-methyl-3-tert.butyl-acetophenone ⟶ dehydration |
| H | 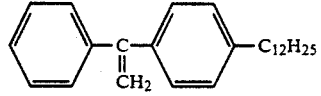 | 175–180° C. 0.1 mbar | Phenylmagnesium bromide + dodecylacetophenone ⟶ dehydration |
| I | 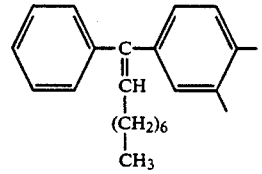 | 180–190° C. 0.015 mbar | Octylmagnesium bromide + dimethylbenzophenone ⟶ dehydration |

The solvents (benzene, methylcyclohexane, heptane, tetrahydrofuran, diethyl ether or. triethylamine) were purified by distillation with sufficient butyllithium and a small amount of styrene as indicator for the color to remain orange.

Dimethyl ether, which boils at −25° C., was obtained from a cylinder, and the gas was purified by being passed through a wash bottle containing secbutyllithium/methylcyclohexane solution and was then passed into the reactor.

Nitrogen was purified with a mixture of white oil, 1% by weight styrene and 5% by weight lithium butyl.

Lithium was used in the form of 1 to 5 mm granules supplied by Merck-Schuchardt.

Commercial butadiene and styrene were purified by distillation with 0.5% by weight triisobutylaluminum for the polymerization experiments.

1,5-Diazabicyclo[3.1.0]hexane, which is described in European patent application 87 103 893 and called propylenediaziridine hereinafter, and commercial ethylene oxide, which was taken from a cylinder and purified by distillation with 0.5% triisobutylaluminum, were used for the functionalization.

Analytical Methods a) Characterization of the initiators according to the invention aa) Determination of the polymerization activity (PA)

The PA is defined as the content of lithium active in the polymerization. 1 mol of bifunctional initiator is thus equivalent to 2 mol of PA.

An amount of solution containing about 2 to 3 mmol of PA is removed from the reactor or the storage vessel using a calibrated 5 ml disposable polypropylene syringe (manufactured by Braun-Melsungen AG, FRG) equipped with a 15 cm needle under inert conditions (impurities are removed from the syringe by filling and emptying with reaction solution several times) and introduced through a rubber cap into a 250 cm$^3$ flask which is flushed with pure nitrogen and in which 100 ml of toluene are stirred with a magnetic stirrer. Impurities in the toluene have previously been removed by titration against the reaction solution until the color is pale yellow. The intensely colored solution is then titrated against 1N isopropanol in absolute toluene from a 5 cm$^3$ calibrated injection syringe until colorless. The total amount of PA in the reactor is then calculated from $$\frac{\Sigma \text{ (cm}^3 \text{ in storage vessel } + \text{ cm}^3 \text{ removed)}}{\text{cm}^3 \text{ removed}} \times \text{cm}^3 \text{ 1N i-propanol} = \text{mmol } PA$$

ab) Determination of the alkali metal content

An amount of initiator solution corresponding to about 1 mmol of PA is removed as described in aa) and added under nitrogen to a mixture of 10 cm$^3$ of cyclohexane and 1 cm$^3$ of methanol. The colorless mixture is then extracted by shaking with 20 cm$^3$ of distilled water. After settling, the clear aqueous extract is removed with an injection syringe, and the solution is extracted twice more with 10 cm$^3$ of water each time. The combined extracts are boiled in an Erlenmeyer flask until the organic solvents have been removed. After cooling, the solution is titrated against N/10 HCl with phenolphthalein until neutral.

$$\frac{\Sigma \text{ (cm}^3 \text{ in storage vessel } + \text{ cm}^3 \text{ removed)}}{\text{cm}^3 \text{ removed} \times 10} \times \text{cm}^3 \text{ N/10 HCl} = \text{mmol of alkali metal}$$

ac) Determination of the ethers or tertiary amines present in the initiator 5 cm$^3$ of the initiator solution containing about 1 to 3 mmol of PA are titrated in a 25 cm$^3$ distillation flask under nitrogen against a 1N solution of isopropanol in toluene until colorless (x cm$^3$). All the solvents are then driven over into a receiver cooled with methanol/carbon dioxide, and the content of ethers or amines in the distillate is determined in % by weight by gas chromatography. A Shimadzu GC-3BT gas chromatorraph with a Carbowax 20M column at 60° C. was used.

The molar ratio of ether to polymerization activity (PA) is calculated from $$\frac{\% \text{ by weight ether or tert. amine} \times (5 + \text{cm}^3 \text{ of 1 N i-propanol used})}{\text{mmol of } PA \times 7.2} = \frac{\text{mmol of ether/tert. amine}}{PA}$$

ad) Determination of the solubility of the initiators

Where the initiator was not insoluble an injection syringe was used to transfer 1 cm$^3$ samples of initiator solution into 10 cm$^3$ of toluene, methylcyclohexane or n-heptane. When the solubility was low, a usually liquid phase separated out. In addition, the color of the supernatant solution was assessed—a deeper color indicates higher solubility.

EXAMPLES 1 to 19

Examples 1 to 19 describe the preparation of initiators according to the invention. The reactor used is a 500 cm$^3$ four-necked flask which is equipped with a magnetic stirrer and thermometer, has a connector closed with a rubber cap and can be flushed with pure nitrogen. The reactor is incorporated in a water bath which can be cooled.

The reactor is charged in each case with highly purified ether or tertiary amine, where appropriate methylcyclohexane or other inert hydrocarbons and about 2.0 g of commercial lithium granules. 50 mmol of the substituted 1,1-diarylethylene are added. At 25° C. the reaction starts immediately or after up to 15 minutes, depending on the purity of the products, with the contents becoming colored and the temperature increasing. The mixture is cooled so that 25° C. is not exceeded. The reaction is complete when the internal and bath temperatures are the same again, generally after from 30 minutes to one hour. The P.A and Li content in the solution are determined. The solution is then transferred under inert conditions, in such a way that unreacted lithium remains in the reactor, into a 250 cm$^3$ distillation flask equipped with an insulated column of diameter 20 mm. The reactor is washed twice with 25 cm$^3$ of methylcyclohexane each time, and the washings are transferred into the distillation flask. The distillation apparatus has previously been purified by boiling with a lithium butyl solution. The reflux condenser is cooled with ice/salt at −20° C. After addition of a further 50 cm$^3$ of methylcyclohexane, the ether or the amine is distilled out of the initiator solution, gradually reducing the pressure, with a reflux ratio of about 1:10 so that the bottom temperature does not exceed 25° C. At the end of the distillation, the top and bottom temperatures are the same.

Table 2 is a compilation of the degree of conversion, the content of polymerization activity (PA) in mol/l, the composition of the initiators and their solubility in 3 important hydrocarbons.

TABLE 2

| Example no. | SDAE[1] (Tab. 1) | pol. sol.[2] | Conversion % of theory | Initiator solution Concentration mol/l PA[12] | Molar ratio PA/PL[2] | Solubility[11] in T[8] | M[9] | n-H[10] |
|---|---|---|---|---|---|---|---|---|
| Comparison | A | PHT[4] | 100% | insoluble[3] | | — | — | — |
| Comparison | B | DEE | 100% | insoluble[3] | | — | — | — |
| Comparison | C | DEE | 100% | colored suspension[3] | | — | — | — |
| Comparison | D | DEE | 100% | colored suspension[3] | | — | — | — |
| 1 | E | DEE | 100% | 1.5 | 0.37[3] | +− | — | — |

TABLE 2-continued

| Example no. | SDAE[1] (Tab. 1) | pol. sol.[2] | Conversion % of theory | Initiator solution Concentration mol/l PA[12] | Molar ratio PA/PL[2] | Solubility[11] in T[8] | M[9] | n-H[10] |
|---|---|---|---|---|---|---|---|---|
| 2 | F | DEE | 100% | oily emulsion 1.75 | 0.2[3] | − | +− | − |
| 3 | F | THF | 100% | 1.83 | 1.63[3] | + | + | +− |
| 4 | G | THF | 100% | 1.70 | 1.52[3] | + | + | +− |
| 5 | G | DEE | 100% | 1.80 | 0.30[3] | + | + | +− |
| 6 | H | DEE | 100% | 0.80 | 0.18[3] | ++ | ++ | ++ |
| 7 | H | DMEA[6] | 100% | 0.75 | <0.05[3] | ++ | ++ | ++ |
| 8 | H | DME[7] | 100% | 0.85 | 0.12[3] | ++ | ++ | ++ |
| 9 | I | THF | 100% | 1.20 | 4.00 | ++ | ++ | ++ |

[1] substituted diarylethylene
[2] polar solvent; also PL
[3] polar solvent distilled out
[4] tetrahydrofuran
[5] diethylethylamine
[6] dimethylethylamine
[7] dimethyl ether
[8] toluene
[9] methylcyclohexane
[10] n-heptane
[11] − insoluble, +− slightly soluble, + soluble, ++ very soluble
[12] polymerization activity

Polymerization

The following analytical methods were used to characterize the polymerization products described in the examples.

ba) Molecular weights and molecular weight distribution by GPC

Non-functionalized samples were used for the analysis. A Waters GPC apparatus was used for the measurements. The molecular weights were determined using calibration plots, comparing with standardized polymers suitable for calibration (cf. G. Glöckner, "Polymercharakterisierung durch Flüssigkeits-chromatographie", Verlag H. Hüthig, Heidelberg, 1982). The measurements were carried out on 0.25% strength solutions in THF at 23° C. and a flow rate of 1.2 cm³/min. The Mn and Mw (number average, weight average) were determined, and from these Mw/Mn was calculated as a measure of the non-uniformity. A computer program developed by Polymer Standard Services, Mainz, FRG, was used for this.

In the case of block copolymers, the molecular weight used as an empirical basis was the arithmetic mean, corresponding to the composition, of the molecular weights from the calibration plots for the two homopolymers.

bb) Determination of the viscosity

The viscosity number (VN) was determined by the DIN 51 562 method in toluene (0.5 g of polymer in 100 cm³ of toluene) at 25° C.

bc) Determination of the nitrogen content

The total nitrogen content was determined by the Kjeldahl method.

bd) Determination of the mechanical properties

The mechanical data (tensile strength at 300% elongation, ultimate tensile strength and elongation at break) were determined on test specimens which had been punched, in accordance with DIN 53 455, from 2 mm-thick films pressed between Teflon disks (pressure 10 bar at 150° C.).

be) Crosslinking with diisocyanate 5 g of the polymer were dissolved in 25 cm³ of dry cyclohexane, and 0.33 mmol of a solution of toluylene diisocyanate (TDI) in cyclohexane was added. After thorough mixing, the mixture was poured onto silicone-coated paper and dried at room temperature.

bf) Degradation of butadiene/styrene block copolymers and determination of the molecular weight of the polystyrene blocks The process for the oxidative degradation of the polybutadiene component with peroxide/osmium tetroxide is described in detail by Ph. Kubin-Eschger, Angew. Makromol. Chem. 26 (1972) 207, so that description is unnecessary here.

bg) Determination of the OH number

The OH number was determined by the re-precipitated polybutadiene oils first being stirred at 140° C. under a pressure of 0.4 mbar until all volatiles had been removed and no further gas was being evolved. About 2 g of the oil were dissolved in highly purified cyclohexane in a 250 cm³ flask under pure nitrogen and mixed with 50 cm³ of THF. After addition of 0.5 cm³ of 1,1-diphenylethylene as indicator, the solution was titrated against a 0.1N solution of n-butyllithium in cyclohexane until a pale orange color appeared. Titration took place through a rubber cap with a calibrated syringe. The blank which had been determined in the same way was subtracted from the amount used.

The method was checked for validity by ¹H-NMR spectroscopy. In the ¹H-NMR spectra of the polybutadienes with OH termini, the methylene protons of the —CH$_2$—OH group appear as a distinct absorption in the region of $\delta = 3.6$ ppm.

The ratio of the intensities of these resonances by comparison with the absorption spectrum of the polybutadiene main chain can be used to calculate the content of OH groups, expressed as the OH number. The method is described, for example, in "Spektroskopische Methoden in der organischen Chemie" by Manfred Hesse, Herbert Meier, Bernd Zeck, Georg Thieme Verlag, Stuttgart—New York, 3rd edition, 1987. Compare also, for example, Polym. J. 17, no. 8, pp. 977 to 980 (Short Comm.).

Polymerization

The reactor used for the polymerization experiments was a 10 l glass flask equipped with a heating and cooling jacket and with a stirrer, a reflux condenser cooled with ice/salt at −30° C., a graduated dropping funnel likewise equipped with an ice/salt reflux condenser, a connector closed with a rubber cap, and an inlet for pure nitrogen. Traces of moisture and oxygen are removed from the nitrogen by washing with white oil containing 2% by weight lithium butyl.

The reactor was initially boiled with a solution of lithium butyl in cyclohexane to which a little styrene had been added. The orange color which acts as indicator of the activity of the solution must be present at the end. The solution was drained off, and the reactor was charged with 3 l of cyclohexane which had previously been purified on a molecular sieve column. Impurities still present were removed by titration at 40° C. against an initiator solution according to the invention through the rubber cap using a calibrated syringe until an orange color appeared.

In Examples 10 to 14, S-B-S 3-block copolymers composed of 27% by weight styrene and 73% by weight butadiene were prepared with a target molecular weight of 60,000. For this, after titration of the contents of the reactor, about 50 cm³ of butadiene and 9 mmol of PA of the particular initiators, plus 9 mmol of lithium t-butylate, were added at 70° to 80° C. and, after the polymerization had started, the remaining butadiene (total 300 cm³ = 187.5 g) was added at about 70° C. so as to maintain gentle reflux.

After the end of the addition, 60° C. was maintained for one hour and, after removal of a sample, 89 cm³ = 81 g of styrene were added and polymerization was continued at from 50° to 60° C. After 60 minutes the mixture was cooled and poured into 5 l of ethanol which contained 0.5% by weight of di-t-butyl-p-cresol. The precipitated polymers were extracted by kneading with alcohol several times and then dried at 60° C. overnight in a vacuum oven.

Table 3 gives the experimental data and analytical measurements for Examples 10 to 14.

Table 4 compares the mechanical properties and the butadiene configuration of Example 11 with a conventionally prepared material.

TABLE 4

| | Mechanical properties and configuration | | | | | |
|---|---|---|---|---|---|---|
| | Tensile strength at 300% elongation [N/mm²] | Ultimate tensile strength [N/mm²] | Elongation at break [%] | Butadiene configuration FTIR[2] | | |
| Ex. no. | | | | % 1,4-trans | % 1,2- | % 1,4-cis |
| 11 | 2.80 | 6.32 | 815 | 45.6 | 22 | 29.3 |
| Comp.[1] | 1.95 | 9.62 | 557 | 57.4 | 12.2 | 30.4 |

[1]The S-B-S 3-block copolymer (27% by weight styrene, 73% by weight butadiene and MW: 68,000) was prepared with lithium butyl by consecutive polymerization of styrene, butadiene and styrene in cyclohexane at 70° C. by known methods.
[2]FTIR = Fourier analysis of the infrared spectra
It is evident from the data that the polymer prepared with the initiator according to the invention has mechanical properties which are at least equivalent.

EXAMPLE 15

Preparation of a polybutadiene oil functionalized with amino end-groups 3000 cm³ of cyclohexane and 50 cm³ of butadiene were placed in the apparatus of Examples 10 to 14, which was, however, equipped with a metal cross-blade stirrer for thorough mixing using a high torque. At 65° C., 16.5 mmol (33 mmol of PA) of the initiator from Example 14 were added, and a further 84 cm³ (total 83 g) of butadiene were run in at a rate such that refluxing was just prevented. After the addition was complete, the mixture was maintained at 60° C. for 30 minutes to complete the polymerization, then cooled to 40° C. and functionalized with 40 mmol of propylenediaziridine, the solution becoming viscous and gel-like. After the contents of the reactor had been stirred for 30 minutes they were precipitated with 20 l of ethanol. The polybutadiene oil was stirred with ethanol three times, mixed with 0.2 g of di-t-butyl-p-cresol and dried at 60° C. under reduced pressure. The result was a pourable polybutadiene oil of Mn 6300 (GPC) and Mw/Mn 1.06. The nitrogen content by the Kjeldahl method was 0.81% (theory: 0.89%). FTIR analysis of the configuration showed 41.4% 1,2, 23.4% 1,4-cis and 35.5% 1,4-trans for the incorporated polybutadiene.

4 mmol of hexamethylene diisocyanate (0.6 g) were rapidly stirred into 5 g of the oil, using a glass rod, in a penicillin tube at room temperature, and the mixture was poured onto silicone-coated paper where it solidified in minutes to give a colorless elastic gum.

TABLE 3

| Preparation of 3-block styrene/butadiene/styrene copolymers Target: Molecular weight 60,000, 27% polystyrene | | | | | | | |
|---|---|---|---|---|---|---|---|
| Analytical data | | | | | OsO₄ degradation polystyrene block Mn × 10⁻³ | | |
| Example no. | Catalyst from Example | GPC: PB block Mn × 10⁻³ | Final product Mn × 10⁻³ | Mw/Mn | Th. | found | Quality of the polymers |
| 10 | 1 | 46.3 | 66.7 | 1.05 | 9.0 | 11.0 | very tough and elastic |
| 11 | 3 | 50.6 | 69.3 | 1.06 | 9.36 | 9.55 | very tough and elastic |
| 12 | 2 | 50.5 | 70.4 | 1.11 | 9.5 | 11.4 | very tough and elastic |
| 13 | 6 | 47.4 | 68.0 | 1.06 | 9.18 | 11.3 | very tough and elastic |
| 14 | 9 | 55.7 | 78.0 | 1.23 | 10.5 | 13.7 | very tough and elastic |

EXAMPLES 16 TO 18

Preparation of polybutadiene oils functionalized with OH groups

The process of Example 15 was carried out but using ethylene oxide for functionalization. This caused an even greater increase in the viscosity than in Example 15, and the mass became like a clear gel. After it had been stirred for 1 h in order to ensure thorough mixing and complete reaction, a few cm³ of methanol were added, resulting in a mobile solution which was then worked up as in Example 15. The table below indicates the amounts and analytical data for Examples 16 to 18.

TABLE 5

| Example | Initiator from Example | mmol of PA | Target molecular weight | Butadiene (g) | GPC analysis | | OH number | |
|---|---|---|---|---|---|---|---|---|
| | | | | | Mn | Mw/Mn | Th.*) | found |
| 16 | 3 | 16.6 | 10,000 | 83 | 11,307 | 1.06 | 10.0 | 11.5 |
| 17 | 4 | 33.0 | 5,000 | 83 | 6,213 | 1.01 | 18.0 | 18.5 |
| 18 | 5 | 33.0 | 5,000 | 83 | 9,736 | 1.12 | 11.5 | 12.0 |

We claim:

1. A process for the preparation of a polymer, comprising contacting a monomer amenable to anionic polymerization selected from the group consisting of vinyl aromatic compounds and conjugated dienes with an organic compound of an alkali metal (M) of formula (I)

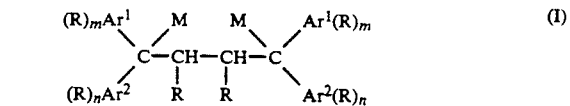

where $Ar^1$ and $Ar^2$ are identical or different aryl or hetaryl radicals which have one or more rings which are either separate or fused, and where R is selected from the group consisting of hydrogen, linear or branched alkyl, aralkyl or cycloalkyl with 1 to 7 or 5 to 25 carbon atoms, with the proviso that at least one R substituent is different from hydrogen that the total of carbon atoms in all the R is at least 3, and m and n are each an integer up to 4.

2. A process for the preparation of a polymer according to claim 5, wherein M is lithium.

* * * * *